United States Patent
Mutsers et al.

(10) Patent No.: US 7,704,419 B2
(45) Date of Patent: Apr. 27, 2010

(54) PROCESS FOR THE PREPARATION OF UREA GRANULES

(75) Inventors: Stanislaus Martinus Petrus Mutsers, Geleen (NL); Antonius Jozef Peter Bongers, Papenhoven (NL); Gerardus Mathias Cornelis Wagemans, Heythuysen (NL)

(73) Assignee: DSM IP Assets B.V., Heerlen (NL)

( * ) Notice: Subject to any disclaimer, the term of this patent is extended or adjusted under 35 U.S.C. 154(b) by 1143 days.

(21) Appl. No.: 10/564,082

(22) PCT Filed: Jul. 2, 2004

(86) PCT No.: PCT/NL2004/000469

§ 371 (c)(1),
(2), (4) Date: Jan. 11, 2006

(87) PCT Pub. No.: WO2005/007619

PCT Pub. Date: Jan. 27, 2005

(65) Prior Publication Data

US 2006/0177574 A1 Aug. 10, 2006

(30) Foreign Application Priority Data

Jul. 17, 2003 (NL) .................................. 1023941

(51) Int. Cl.
*B29B 9/10* (2006.01)
*C05C 9/00* (2006.01)

(52) U.S. Cl. ............................ 264/12; 71/28; 71/64.06; 422/243

(58) Field of Classification Search ...................... 71/28, 71/64.06; 264/12; 427/213
See application file for complete search history.

(56) References Cited

U.S. PATENT DOCUMENTS

| | | | | |
|---|---|---|---|---|
| 3,036,338 A | * | 5/1962 | Nack | 264/7 |
| 3,117,020 A | * | 1/1964 | Temistoche et al. | 427/213 |
| 3,463,098 A | * | 8/1969 | Gyde et al. | 264/117 |
| 3,475,132 A | * | 10/1969 | Chen et al. | 34/585 |
| 3,844,726 A | * | 10/1974 | Denaeyer et al. | 23/301 |
| 4,190,622 A | * | 2/1980 | Landis | 264/14 |
| 4,217,127 A | * | 8/1980 | Kono et al. | 71/28 |
| 4,219,589 A | | 8/1980 | Niks et al. | |
| 4,261,958 A | * | 4/1981 | Pevzner et al. | 423/121 |
| 4,525,198 A | * | 6/1985 | Van Hijfte et al. | 71/28 |
| 4,946,653 A | * | 8/1990 | Stopp et al. | 422/140 |
| 5,653,781 A | * | 8/1997 | Kayaert et al. | 71/28 |
| 6,159,252 A | * | 12/2000 | Schutte et al. | 23/313 FB |
| 7,029,504 B2 | * | 4/2006 | Rabie et al. | 23/313 FB |

FOREIGN PATENT DOCUMENTS

WO  WO 94/03267  2/1994

OTHER PUBLICATIONS

Bruynseels, "Granulate in fluid bed", Hydrocarbon Processing, Sep. 1981, pp. 203-208.
International Search Report.

* cited by examiner

*Primary Examiner*—Wayne Langel
(74) *Attorney, Agent, or Firm*—Nixon & Vanderhye P.C.

(57) ABSTRACT

Process for the preparation of urea granules in a fluid bed granulator comprising at least one inlet for fluidization air, a distribution plate above which the fluid bed is present and sprayers that are mounted in the distribution plate, from which the urea melt is sprayed on or over the urea particles present in the fluid bed, which particles are kept in motion by the fluidization air, characterized in that the fluidization air contains very finely atomized water and in that the urea concentration of the urea melt is higher than 97 wt. %.

12 Claims, No Drawings

PROCESS FOR THE PREPARATION OF UREA GRANULES

This application is the US national phase of international application PCT/NL2004/000469 filed 2 Jul. 2004 which designated the U.S. and claims benefit of NL 1023941, dated 17 Jul. 2003, the entire content of which is hereby incorporated by reference.

The invention relates to a process for the preparation of urea granules in a fluid bed granulator comprising at least one inlet for fluidization air, a distribution plate above which the fluid bed is present and sprayers that are mounted in the distribution plate, from which the urea melt is sprayed on or over the urea particles present in the fluid bed, which particles are kept in motion by the fluidization air.

Such a process is described in 'Granulate in Fluid bed', Hydrocarbon Processing, September 1981, pages 203-208.

This publication describes a process for the preparation of urea granules in a fluid bed whereby a urea solution with a concentration of 95-97 wt. % is sprayed in the form of very fine droplets. In the granulator these fine droplets come into contact with the urea particles present in the fluid bed causing the urea particles to grow. The concentration of the urea solution of 95-97% implies that the urea solution still comprises much water. The evaporation of this water ensures cooling during granulation.

A significant drawback of this process is that as the water evaporates out of the sprayed droplets of urea melt there evolves relatively much fine urea dust that is blown out of the fluid bed along with the fluidization air. It is desirable for this urea to be recovered from the off-gas for economic reasons and to protect the environment.

It is the aim of the invention to provide a process that does not have this drawback.

The invention is characterized in that the fluidization air contains very finely atomized water and in that the urea concentration of the urea melt is higher than 97 wt. %.

This ensures that the water can evaporate very rapidly, so achieving the desired cooling by evaporation of water without the formation of large amounts of fine dust.

An advantage of the invention also is that the water can be introduced into the granulator in various locations so that the optimal location for atomization of water in the fluidization air can be freely chosen.

The process according to the invention comprises the preparation of urea granules in a fluid bed granulator.

Such a granulator comprises an inlet for fluidization air. The fluidization air is used for keeping the particles that make up the fluid bed in a fluidized state. The fluidization air is introduced in the granulator below the distribution plate and is discharged from the top of the granulator whether or not after being filtered. The superficial velocity of the fluidization air in the fluid bed is normally between 1.5 and 4 m/s.

A distribution plate is present in the granulator. The fluid bed of urea particles is present above the said plate. Urea melt is sprayed from sprayers mounted in the distribution plate on or over the urea particles present in the fluid bed, which particles are kept in motion by fluidization air. Any suitable sprayers may be used as the sprayers from which the urea melt is sprayed. Examples of such sprayers are the sprayers described in the above-mentioned article in Hydrocarbon Processing and in U.S. Pat. No. 4,619,843. The sprayers for the urea melt utilize a secondary air flow in the sprayer itself for spraying the melt.

The number of sprayers for spraying the urea melt may vary from for example 5 to 25 per $m^2$ of distribution plate.

Fluidization air is introduced in the fluid bed granulator below the distribution plate through one or more supply lines. The fluidization air in the granulator contains very finely atomized water that is added to the fluidization air. This addition may be effected in the granulator in various locations and in various ways.

The finely atomized water may, for example, be added to the fluidization air below the distribution plate. This may be achieved by positioning sprayers in the underside of the granulator, but also by atomizing water in the supply lines for fluidization air.

The water may also be added to the fluidization air at the elevation of the distribution plate or just above the distribution plate. It is preferred to add the water to the fluidization air at 0-50 cm above the distribution plate, more preferably 5-15 cm above the distribution plate. The water may also be added to the fluidization air through atomization from sprayers in the distribution plate.

Most preferably, the water is added to the fluidization air by atomization of water in one or more supply lines for fluidization air. This is effected by atomization of water from one or more sprayers in the supply line. Preferably, this is one sprayer that is positioned at the centre of the supply line.

The sprayers are preferably positioned some meters away from the outflow of the supply line in the granulator.

If the water is atomized in one or more supply lines for fluidization air, the atomized water may be distributed highly homogeneously in the granulator using as few sprayers as possible.

Water is sprayed using sprayers that are capable of atomizing the water very finely. Preferably, the water is so atomized that the maximum droplet size of the atomized water is less than 50 µm; more preferably less than 40 µm and most preferably less than 20 µm.

The smaller the water droplets, the more rapidly the water will evaporate during granulation and the more effective the cooling will be. Effective cooling during granulation ensures that either the granulator can be designed to have smaller dimensions or the granulator throughput can be increased. The process of the invention allows 10-50 wt. % more urea granulate to be produced in a granulator of the same size.

Because of the small droplet size of the atomized water it is possible that, when the water is sprayed in a supply line for fluidization air, the droplets are completely evaporated when the fluidization air enters the granulator. The fluidization air will than be saturated with water when it enters the granulator.

As the sprayers for spraying water use may be made of any sprayers provided that the maximum droplet size of the atomized water is less than 50 µm. Examples of such sprayers are two-phase sprayers and sonic sprayers. Additionally, the water may be atomized by what is known as flashing water that is above the boiling point.

The water is normally sprayed at a temperature of between 0 and 150° C., preferably between 15 and 90° C. and at a pressure of between 0.2 and 5.0 MPa.

The urea concentration of the urea melt is higher than 97 wt. %; preferably higher than 98 wt. %. A high urea concentration of the melt has the advantage that urea granulate is formed whose water content is extremely low. The urea granulate contains 0.3 wt. % of water as a maximum.

The fluidization air that leaves the granulator contains less than 2 wt. % of urea dust relative to the melt quantity supplied to the granulator.

The invention also relates to a granulator for granulating urea, comprising an inlet for fluidization air, a distribution plate above which the fluid bed is present and sprayers mounted in the distribution plate, from which the urea melt is sprayed.

Such a granulator Is described in 'Granulate in Fluid bed', Hydrocarbon Processing, September 1981, pages 203-208.

In the granulator according to the prior art a urea melt is sprayed with a concentration of 95-97 wt. %. If the urea concentration of the urea melt increases, the capacity of the granulator decreases.

It has now surprisingly been found that a urea melt with a urea concentration higher than 97 wt. % can be sprayed in such a granulator without the capacity decreasing.

This is possible if the granulator comprises sprayers that are mounted below, in or above the distribution plate from which water is atomized in the fluidization air. In such a granulator it is even possible to increase the capacity while spraying a urea melt with a urea concentration higher than 97 wt. %.

The water may be sprayed in the granulator at various locations and in various ways.

The finely atomized water may, for example, be added to the fluidization air below the distribution plate. This may be achieved by positioning sprayers in the underside of the granulator, but also by atomizing water in the supply lines for fluidization air.

The water may also be added to the fluidization air at the elevation of the distribution plate or just above the distribution plate. It is preferred to add the water to the fluidization air at 0-50 cm above the distribution plate, more preferably 5-15 cm above the distribution plate. The water may also be added to the fluidization air through atomization from sprayers in the distribution plate.

Most preferably, the water is added to the fluidization air by atomization of water in one or more supply lines for fluidization air.

This is effected by atomization of water from one or more sprayers in the supply line. The sprayers are preferably positioned some meters away from the outflow of the supply line in the granulator.

As the sprayers for spraying the water use may be made of the sprayers described above.

The sprayers for the atomization of water may be mounted when a granulator is being built but may also be added when an existing granulator is being revamped.

An advantage of revamping an existing granulator according to the process of the invention is that the capacity of the existing granulator can be increased.

The invention will be further elucidated by means of the examples without being restricted thereto.

EXAMPLE I

A fluid bed granulator is divided into a granulation section and a cooling section. Fluidization air is supplied to both sections.

Urea nuclei are supplied to the first compartment of the granulation section. The urea particles are sprayed with urea melt. During their stay in the granulator the particles grow to form granules of the required diameter.

Next the product is cooled in the cooling section and separated by screening into three fractions: coarse, desired and fine.

The desired product, urea granules of the desired size, is transported to storage. The coarse product, after being crushed, is returned to the first compartment of the granulation section along with the fine product, where it is supplied as urea nuclei.

A stream of nuclei was supplied to the first compartment of the granulation section of a fluid bed granulator at a flow rate of 9073 kg/hour. These particles were sprayed with urea melt of 140° C., flow rate 15861 kg/hour, that was sprayed through multiple sprayers. Spraying the urea melt required 6979 kg of air at 140° C. per hour. The urea melt contained 98.5 wt. % of urea. The temperature of the fluid bed was 105° C.

During granulation, the flow rate of the fluidization air of 36° C. was 36957 kg/hour. To the fluidization air for the granulation was added 350 kg/hour of water by atomizing water in the supply line for fluidization air. Approx. 2.5 wt. % of water relative to the quantity of urea melt was added in this way.

The droplet size of the water was less than 20 μm.

After the granules had passed through the granulation section a product stream of 24434 kg/hour was obtained.

After screening, there were obtained 15120 kg/hour of desired end product, a coarse product stream of 1815 kg/hour and a fine product stream of 7258 kg/hour. The two latter streams were returned to the first compartment of the granulation section.

COMPARATIVE EXPERIMENT A

Urea was granulated as described in Example I except that no water was added.

12238 kg of urea melt/hour was added under the same conditions. Spraying the urea melt now required 5385 kg of air/hour.

The amount and temperature of the fluidization air and the amount and temperature of the air to the cooling section are the same as in Example I. As in Example I, a fluidization temperature of 105° C. was reached.

After the granules had passed through the granulation section, a product stream of 18854 kg/hour was obtained.

After screening, there were obtained 11667 kg/hour of desired final product, a coarse product stream of 1400 kg/hour and a fine product stream of 5600 kg/hour. The two latter streams were returned to the first compartment of the granulation section; meaning that a stream of 7000 kg/hour of nuclei were supplied to the first compartment.

The quantity of desired end product is approx. 30 wt. % less than according to the process in Example I.

The invention claimed is:

1. Process for the preparation of urea granules in a fluid bed granulator comprising:
   forming a fluid bed of urea particles above a distribution plate in a fluid bed granulator by introducing fluidization air containing very finely atomized water droplets through at least one inlet of the granulator; and
   spraying a urea melt having a concentration of urea therein of higher than 97 wt. % from sprayers of the granulator so that the urea melt is sprayed on or over the urea particles present in the fluid bed, wherein the urea particles are kept in motion by the fluidization air.

2. Process according to claim 1, wherein the fluidization air contains 0.0001-10 wt. % of water relative to the sprayed amount of urea melt.

3. Process according to claim 1, comprising adding the water droplets to the fluidization air below the distribution plate.

4. Process according to claim 1, comprising adding the water droplets to the fluidization air in one or more supply lines for the fluidization air.

5. Process according to claim 1, comprising adding the water droplets to the fluidization air by atomization from one or more sprayers in the supply line for the fluidization air.

6. Process according to claim 1, comprising adding the water droplets to the fluidization air at or just above an elevation of the distribution plate in the granulator.

7. Process according to claim 6, comprising adding the water droplets to the fluidization air at 0-50 cm above the distribution plate.

8. Process according to claim 1, wherein the maximum size of the atomized water droplets is less than 50 μm.

9. Process according claim 1, wherein the urea concentration of the urea melt is higher than 98 wt. %.

10. Process according to claim 1, wherein the total amount of urea dust in the fluidization air leaving the granulator is less than 2 wt. % of the amount of the urea melt supplied to the granulator.

11. Process for revamping a granulator for the granulation of urea comprising an inlet for fluidization air, a distribution plate above which the fluid bed is present and sprayers that are mounted in the distribution plate, from which the urea melt is sprayed, the process comprising mounting water atomizers below, in or above the distribution plate and introducing water droplets into the fluidization air by atomizing water through the water atomizers.

12. Process according to claim 11, wherein the water atomizers are mounted in one or more supply lines for the fluidization air.

* * * * *